US006248355B1

(12) United States Patent
Seth

(10) Patent No.: US 6,248,355 B1
(45) Date of Patent: *Jun. 19, 2001

(54) PHARMACEUTICAL COMPOSITION CONTAINING AN ACID-LABILE OMEPRAZOLE AND PROCESS FOR ITS PREPARATION

(75) Inventor: Pawan Seth, Irvine, CA (US)

(73) Assignee: Schwarz Pharma AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/538,845

(22) Filed: Dec. 30, 1999

Related U.S. Application Data

(63) Continuation of application No. 09/043,145, filed on Aug. 3, 1998.

(30) Foreign Application Priority Data

| Sep. 21, 1995 | (FR) | 95/11094 |
| Dec. 7, 1995 | (FR) | 95/14492 |
| Feb. 23, 1996 | (FR) | 96/02265 |
| Apr. 23, 1996 | (FR) | 96/05082 |

(51) Int. Cl.$^7$ ............... A61K 9/54; A61K 9/22; A61K 9/28; A61K 9/48
(52) U.S. Cl. ............ 424/458; 424/464; 424/451; 424/468; 424/472; 424/474
(58) Field of Search ............... 424/458, 459, 424/461, 462, 464, 468, 469, 470, 489, 490, 493, 494, 495, 451

(56) References Cited

U.S. PATENT DOCUMENTS

| 5,126,145 | 6/1992 | Evanstad et al. ............... 424/465 |
| 5,133,974 | 7/1992 | Paradissis et al. ............. 424/480 |
| 5,250,527 | 10/1993 | Ife ............................... 514/234.5 |
| 5,374,730 | 12/1994 | Slemon et al. ................. 546/271 |
| 5,399,700 | 3/1995 | Min et al. ...................... 546/271 |
| 5,626,875 | 5/1997 | Ballester Rhodes et al. .... 424/464 |
| 5,753,265 | 5/1998 | Bergstrand et al. ............ 424/474 |
| 5,817,338 | * 10/1998 | Bergstrand et al. . |
| 5,840,332 | * 11/1998 | Lerner et al. . |
| 5,945,124 | * 8/1999 | Sachs et al. . |

FOREIGN PATENT DOCUMENTS

| 0 519 144 | 12/1992 | (EP) ................... A61K/9/54 |
| 99/32091 | * 7/1999 | (WO) . |

* cited by examiner

*Primary Examiner*—Thurman K. Page
*Assistant Examiner*—Brian K. Seidleck
(74) *Attorney, Agent, or Firm*—Marshall, O'Toole, Gerstein, Murray & Borun

(57) ABSTRACT

A composition, particularly adapted for oral administration, containing omeprazole, and a method for preparing the composition, are disclosed. The composition, being exempt of alkaline-reacting compounds, contains a core constituted of nuclei and said benzimidazole, the nuclei and benzimidazole being compressed together, an intermediate layer, and an enteric layer.

31 Claims, 7 Drawing Sheets

PHARMACEUTICAL COMPOSITION CONTAINING AN ACID-LABILE OMEPRAZOLE AND PROCESS FOR ITS PREPARATION

CROSS-REFERENCE TO RELATED APPLICATION

This application is a continuation of application Ser. No. 09/043,145, filed Aug. 3, 1998, pending.

BACKGROUND OF THE INVENTION

This present invention relates to a novel composition containing an acid-labile benzimidazole, and to its preparation. This novel composition is perfectly suitable for oral administration. The invention also relates to a process for preparing this composition.

Many substances, of pharmaceutical value, that are labile in an acid medium have been described in the literature. The substances disclosed in the following patents can be given by way of example: EP 244 380, U.S. Pat. No. 4 045 563, EP-0 005 129, BE-898 880, GB-2 141 429, EP-0 146 370, GB-2 082 580, EP-A-0 173 664, EP-A-0 080 602, EP-0127 763, EP-0 134 400, EP-0 130 729, EP-0 150 586, DE-34 15971, GB-2 082 580, SE-A-8504048-3 and U.S. Pat. No. 4 182 766. On the other hand, omeprazole, which is of the family of benzimidazoles, corresponding to an anti-ulcer substance, used conventionally for decreasing gastrointestinal acid secretion, is well known and has been notably discussed in Swedish patent application 78.04231 filed on Apr. 14, 1978, as well as in numerous other patents. Pantoprazole and lansoprazole which both correspond to anti-ulcer substances of the omeprazole family, are notably discussed in U.S. Pat. No. 4,758,579 and in U.S. Pat. No. 4,628,098 respectively.

Chemical substances that are easily destroyed in an acid medium (which is expressed herein by the term "acid-labile" and meaning chemical substances that are labile in an acid medium), such as benzimidazoles and, in particular, omeprazole, lansoprazole and pantoprazole, create a special problem for formulators when it is required to provide a pharmaceutical form designed for oral administration. The product does indeed come into contact with the stomach content, which is a highly acid medium, leading to breakdown of these chemical substances.

In order to avoid contact between the substances and the acid gastric juice following oral administration of the substance, a pharmaceutical formulation is conventionally used, such as a capsule or table which contains a core (tablet, microgranule, pellet, etc . . . containing the acid-labile active substance and an outer layer that surrounds this core and which consists of a gastro-resistant composition that is entero-soluble. Generally, the coating agent is a compound that is particularly insoluble in an acid medium, but which is soluble in a neutral or alkaline medium.

For substances that are highly labile in an acid medium but which are more stable in a neutral or alkaline medium, such as omeprazole, pantoprazole and lansoprazole, it is necessary to add an inert substance to the composition, which leads to an alkaline reaction aimed at improving stability of the active substance during manufacture thereof, and during storage of the pharmaceutical form.

Several prior art documents describe such compositions that are suitable for oral administration of acid-labile substances.

EP-0,244,380 discloses pharmaceutical formulations that are suitable for oral administration of acid-labile substances. It is stated that these acid-labile substances intended for oral administration must be protected by an enteric coating, but conventional enteric coatings of an acid nature are not suitable for this purpose. If one were indeed to cover acid-labile substances which such coatings, the substance would be rapidly decomposed due to direct or indirect contact with the coating, which manifests itself by a change of color and a decrease in the active substance content with the passage of time. The solution proposed in that patent corresponds to formulations consisting of: (a) a core in the form of small particles, i.e. pellets or compressed powder, containing the active substance along with an alkaline reacting compound, (b) one or several inert intermediate layers containing excipients for tablets which are soluble, and which rapidly disintegrate in water, water-soluble film-forming polymer compounds optionally containing alkaline compounds acting as a pH buffer between the core having an alkaline reaction and the outer layer, and (c) an outer layer consisting of an enteric composition. It is also stated that, in order to improve storage stability, the cores containing the active substance should also contain constituents having an alkaline reaction, and that the water that enters by diffusion, or the gastric juice, will dissolve part of the core close to the enteric coating, forming an alkaline solution at this level inside the coated form for administration. This patent claims pharmaceutical formulations containing acid-labile active substances of formula I with the notable exception of omeprazole.

EP-A-0,247,983 which is related to pharmaceutical formulations that are suitable for oral administration of acid-labile substances adopts the general principles developed in EP-A-0,244,380 in order to more particularly apply them to the case of omeprazole. The main claim in that application thus covers the association of omeprazole with an auxiliary alkaline-reacting substance.

U.S. Pat. No. 4,786,505 discloses novel stable preparations containing omeprazole intended for oral administration, their preparation and a method for treating gastrointestinal sicknesses using these novel preparations. These oral pharmaceutical preparations comprise: (a) a core comprising omeprazole and an alkaline reacting compound, an alkaline salt of omeprazole and an alkaline-reacting compound or an alkaline salt of omeprazole alone; (b) at least one inert intermediate layer that is water-soluble or rapidly disintegrates in water; and (c) an external layer comprising an enteric coating.

EP-A-0,519,365 discloses pharmaceutical formulations that are suitable for oral administration of pantoprazole, comprising an acid-labile substance. In order to improve stability of pantoprazole formulations, this document discloses the use of the active substance in a salt form. The pharmaceutical formulations disclosed comprise: (a) a core containing the active principle in a salt form, (b) at least one water-soluble intermediate layer and (c) an outer layer corresponding to an enteric coating. It is stated hat the use of a salt form in the core enables an alkaline environment to be created that protects the active substance. If the salt form does not have a sufficient effect on the pH, it is necessary to add a constituent that has an alkaline reaction to the core.

EP-A-0,519,144 discloses a novel process for producing a stable preparation containing omeprazole, intended for oral administration. This document notably discloses a process for preparing pellets containing omeprazole in which a core constituted of inert substances is covered by the active substance in finely divided form and dispersed in an aqueous dispersion buffered to a pH of 7.0, after which an enteric coating is applied, the finished product being placed inside a capsule.

U.S. Pat. No. 5,232,706 discloses novel stable pharmaceutical preparations containing omeprazole, intended for oral administration. The pharmaceutical compositions disclosed comprised: (a) a core containing omeprazole and an alkaline salt of omeprazole mixed with a first alkaline-reacting compound; (b) at least one intermediate layer formed by an excipient and a second alkaline-reacting compound and (c) an outer layer formed by an enteric coating. It is stated that the problem of the poor stability of the omeprazole is resolved, firstly, by increasing the way the core behaves as a base either by introducing omeprazole in the form of an alkali metal or alkaline-earth salt, or a mixture of omeprazole with a basic compound or by a combination of these two possibilities; and secondly "by incorporating an intermediate layer between the core and the enteric coating for preventing the alkaline core from causing breakdown of the enteric coating".

FR-A-2,692,146 discloses stable compositions of microgranules of gastro-protected omeprazole as well as their preparation. This documents particularly discloses a stable microgranule formulation of omeprazole comprising a neutral core consisting of sugar and starch covered with an active layer constituted by omeprazole diluted in mannitol in substantially equal amounts, and an intermediate layer comprising mannitol; an outer layer formed from an enteric coating being optionally present. There, it is indicated that the omeprazole is employed in a diluted powder form in an amount that is substantially equal to the amount of mannitol in order co protect the omeprazole from contact with solvents and with traces of water present in the binder solutions employed for applying the mixture of omeprazole and mannitol to the neutral grains consisting of sugar and starch. Additionally, according to that patent, supplementary protection of the omeprazole applied co neutral grains is obtains by means of a second protective layer consisting of mannitol and a binder solution in order to definitively isolate the core onto which the omeprazole and the mannitol is applied. This supplementary protection isolates the omeprazole from the outer coating layer that is designed to ensure gastroprotection of the active cores.

WO96/01624 in the name of ASTRA discloses a tableted dosage form comprised of individually enteric coated layered units of a core material comprising a benzimidazole ingredient. Said individually enteric coated layered units are mixed with tablet excipients and compressed together. Said tablet excipients are e.g. microcrystalline cellulose. The resulting tablet is aid to withstand acidic environment.

SUMMARY OF THE INVENTION

The applicant has studied possible novel pharmaceutical compositions designed for oral administration of acid-labile substances, and notably omeprazole, pantoprazole, lansoprazole, leminoprazole and pariprazole, which have excellent storage stability together with stability during their preparation process, and has surprisingly found novel compositions that are particularly stable that do not include either alkaline-reacting compounds nor mannitol in a substantially stoechiometric amount, which are both stated as being essential in the prior art.

Thus, the present invention provides a composition exempt of alkaline-reacting compounds comprising:
(a)—a core containing an acid-labile benzimidazole active principle, said core being constituted of nuclei and said active ingredient mixed together and then compressed together, and said active principle not being in the form of an alkaline salt;
(b)—an intermediate layer; and
(c)—an enteric layer.

According to one embodiment, said nuclei and said active ingredient are granulated together and then compressed together.

According to one preferred embodiment, the nuclei have a particle size, in the absence of the active principle, comprised between 80 and 500 µm, preferably comprised between 150 and 300 µm.

According to a preferred embodiment, in the composition, pharmaceutical excipients, preferable at least one lubricant, are additionally present with said nuclei and said active ingredient.

According to another embodiment, at least one lubricant selected from the group comprising: sodium stearylfumarate, magnesium stearate, glyceryl behenate and talc is additionally present with said nuclei and said active ingredient.

According to another embodiment, the intermediate layer contains silicium dioxide.

Omeprazole, lansoprazole, pantoprazole, leminoprazole or pariprazole are examples of acid-labile benzimidazole active principle.

The invention also provides a method for preparing a composition according to the invention, comprising the steps of:
(i) mixing nuclei with an active principle;
(ii) compressing the product of step (i) to form a core containing an active principle;
(iii) coating said core with an intermediate layer; and
(iv) coating a product from step (iii) with an enteric layer.

According to an embodiment, step (i) is granulation.

According to another embodiment, said step (i) is carried out by spraying a medium containing an active principle onto nuclei in a fluidized bed granulator followed by drying the product thus obtained.

The medium containing the active principle is preferably an aqueous medium.

According to another embodiment, the instant process additionally comprises the step of mixing nuclei or the product of step (i) with pharmaceutical excipients, preferably with at least one lubricant.

The invention will now be described in detail with reference to the attached drawings in which:

DETAILED DESCRIPTION

Here, the expression "acid-labile substance" should be taken to mean substances the breakdown half-life of which is less than 10 minutes and/or is comprised substantially between 10 minutes and 65 hours in aqueous solutions having, respectively a pH less than 4 and/or a pH of 7. Typically, the active principles disclosed in EP 244,380 can be cited as examples, and notably omeprazole, pantoprazole, lansoprazole, leminoprazole and pariprazole.

Here, the expression "benzimidazole active principle" should be taken to mean benzimidazole derivatives that are of therapeutic value. The benzimidazole active principles disclosed in the description notably comprise omeprazole, pantoprazole, lansoprazole, leminoprazole and pariprazole together with benzimidazole derivatives described in EP 244 380, U.S. Pat. No. 4 045 563, EP-0 005 129, BE-898 880, GB-2 141 429, EP-0 146 370, GB-2 082 580, EP-A-0 173 664, EP-A-0 080 602, 30 EP- 0127 763, EP-0 134 400, EP-0 130 729, EP-0 150 586, DE-34 15971, GB-2 082 580, SE-A-8504048-3 and U.S. Pat. No. 4 182 766. In this invention, are described preferably the compounds stated as being preferred in those documents and in particular omeprazole, pantoprazole, lansoprazole, leminoprazole and pariprazole; the alkaline salt form of the active principles cited above being excluded. Derivatives, such as salts (hydrates, etc.), esters and the like (including pro-drugs), are also contemplated, inasmuch as they are not of alkaline nature.

Mixtures of active principles are also envisaged, for example those comprising a benzimidazole in association with another active principle, or those containing two benzimidazoles.

Here, the expression "exempt of alkaline-reacting compound" should be taken to mean a composition that substantially does not contain any alkaline-reacting compound, in other words a composition in which the amount of alkaline-reacting compound is not sufficient to set up an alkaline micro-environment around the active principle when it is in contact with an acid or neutral aqueous medium, for example a micro-environment having a pH above 7.

According to this invention the core consists of a set of nuclei based on pharmaceutical-inert excipients with which the acid-labile active principle has been mixed, i.e. purely mixed, deposited, coated, aggregated, and then having been compressed together.

The expression "nuclei and active ingredient mixed together and then compressed together" covers various embodiments.

Figure 3:
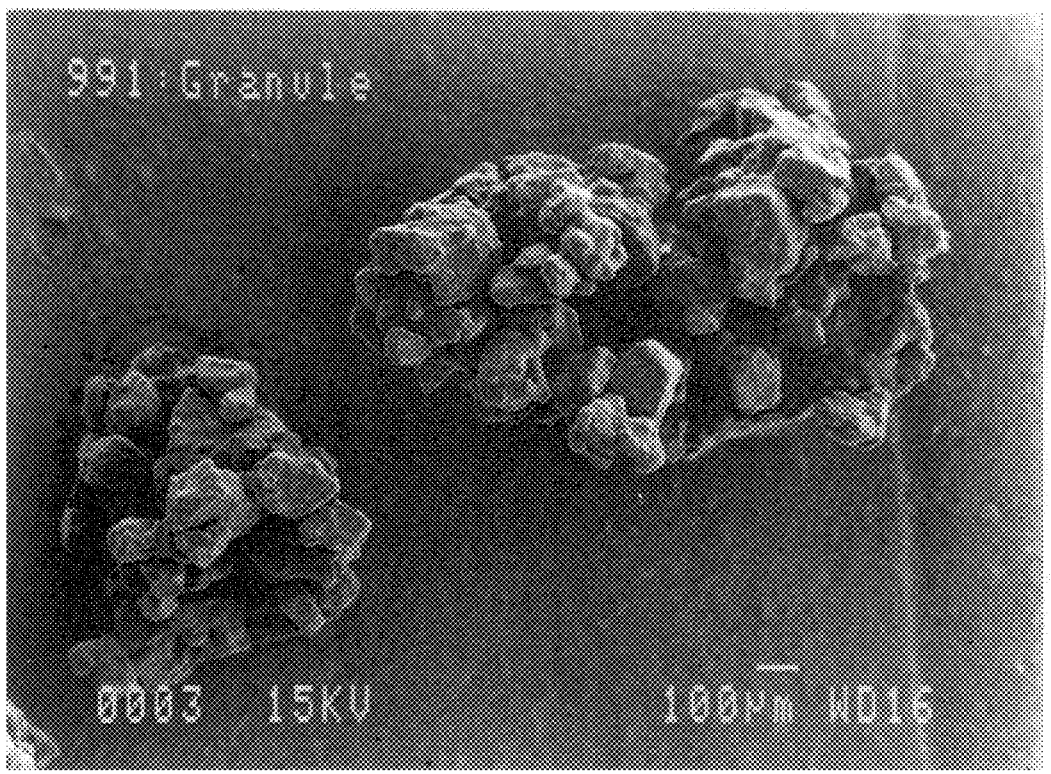
FIG. 3 is a photograph of granules obtained by fluidized bed granulation according to the examples.

According to one embodiment, the process used for the manufacture of the instant cores is granulation, preferably fluidized bed granulation. One skilled in the art is fully aware of that technique. Elements of interest regarding said process may however be found in the publication of Schaefer & Worts, Arch. Pharm. Chemi. Sci., Ed5, 1977, 51–60. According to said granulation technique, the nuclei, e.g. lactose, are fluidized together with the inlet air, and a (binder) solution of the active ingredient is sprayed on the fluidized bed. Granules are then formed of nuclei and active ingredient; said granules are more specifically shown in FIG. 3. It can be seen that the solution formes a binder that holds together several nuclei; agglomeration also occurs between nuclei and/or between benzimidazole particles. Said granules, which can be considered as intermediates, are then compressed together.

Alternative embodiments may be used, e.g. where the active ingredient is present onto the nuclei, which are then compressed together, or where the active ingredient and/or the nuclei are (partially) subject to agglomeration, and then agglomerated nuclei and/or agglomerated active ingredient and nuclei with active ingredient onto same are compressed together.

Another process that may be used for the manufacture is the tank coating technique, where the nuclei are introduced into a solution of the active ingredient, and the resulting slurry is compressed, optionally after a preliminary drying step.

Another way to express the technique for manufacturing the nuclei+active ingredient is to call it "coating technique", since a lot of possible embodiments lead to products that can be qualified as "coated products". Thus, in the instant description, the term "coating step" may be used in lieu of the term "mixing step".

In fact, on a macroscopic scale, the core may be considered as a core having dispersed therein the active ingredient.

Here, the expression "a pharmaceutically-acceptable inert excipient" should be taken to mean a compound that does not lead to a chemical reaction under operating conditions employed that can lead to breakdown of the active principle.

The nuclei can be any substance that is pharmaceutically inert vis-a-vis the active principle and can be crystalline or amorphous. These nuclei may, in general, be composed of a sugar, such as lactose, saccharose, corn starch etc. or any one of the mixtures thereof. The active principle which is optionally mixed with pharmaceutical excipients, is applied to the nuclei using any conventional coating technique employed, for example, in a suitable coating tank or in a fluidized bed device such as a granulator, with the use of suitable aqueous and/or organic solvents, or using a dry process. Coating is preferably carried out in a fluidized bed granulator. Typically Polysorbate 80 or sodium lauryl sulfate mixed with the active principle are added. Preferably, a lubricant, and notably sodium stearylfumarate or magnesium stearate or glyceryl behenate (Ompritol 888 ATO) or (micronized) talc are added after the active principle has been deposited on the inert nuclei. Any conventional excipients used in the pharmaceutical and chemical field that are compatible with the active principle may be used, such as binders, fillers, plastifiers, surfactants, pigments, disintegrating agents, lubricants, wetting agents, etc., excepting alkaline-reacting compounds. The following can be cited as examples of excipients suitable for use in the present invention: polysorbate 80 (Tween®80), sodium lauryl sulfate, hydroxypropylcellulose, hydroxypropylmethylcellulose, talc, microcrystalline cellulose, colloidal silica, polyvinylpyrrolidone, sodium stearylfumarate, magnesium stearate, titanium dioxide, etc.

The intermediate layer, according to the invention consists of at least one sub-layer. It corresponds to one or several inert water-soluble layers or layers which rapidly disintegrate in an aqueous medium, containing non-acid inert pharmaceutical excipients. This layer comprises at least one polymer conventionally used in applications where a film is provided by coating such as: sugars, polyethyleneglycol, polyvinylpyrolidone, poly(vinyl alcohol), hydroxypropylcellulose, hydroxymethylcellulose, hydroxypropylmethylcellulose, etc. The intermediate layer can additionally contain any one of the conventional pharmaceutical excipients cited in the section relating to the core, or a mixture thereof, and notably silicon dioxide. This silicon dioxide is present in an amount which can vary between 2 and 45% by weight based on the dry weight of the intermediate layer, preferably 5 to 18% by weight, for example about 9%.

This intermediate layer is applied to the core using any coating technique conventionally employed in a suitable coating tank or in a fluidized bed device, with the use of suitable aqueous and/or organic solvents, or by using latex suspensions of said excipients.

The enteric layer according to this invention corresponds to a layer that is entero-soluble and gastro-resistant. It is applied to the intermediate layer by conventional coating techniques such as coating in a tank or a fluidized bed employing polymer solutions in water or in suitable organic solvents or using latex suspensions of these polymers. As a polymer, use can be made of: cellulose acetyl phthalate, hydroxypropyl-methylcellulose phthalate, polyvinyl phthalate acetate, methacrylic acid methyl esters/methacrylic acid copolymers, such as for example, compounds known under the Eudragit®L12.5 or Eudragit®L100 (Röhm Pharma) trademarks, or similar compounds conventionally employed for the preparation of enteric coatings, as well as mixtures thereof.

The enteric coating can also be applied using aqueous dispersions of polymers, for example Aquateric® (FMC Corporation), Eudragit®L100-55 (Röhm Pharma), CE5142 coating (BASF). The enteric layer can also contain a pharmaceutically-acceptable plastifying agent such as, for example, ketanol, triacetine, citric acid esters such as those known under the Citroflex® (Pfizer) trademarks, phthalic acid esters, dibutylsuccinate or any other similar plastifying agent. The amount of plastifying agent is in general optimized for each polymer and generally represent 1 to 30% of the polymer, for example from 5 to 20%. Supplementary agents such as talc, pigments, coloring agents, flavoring agents, as well as any other excipient that conventionally enters into the composition of enteric coatings can be employed.

The compositions according to the present invention generally comprise a core representing 40 to 90% by weight, preferably 60–70% by weight based on the total weight of the composition, an intermediate layer representing 5 to 30% by weight, preferably 15 to 20% by weight, based on the total weight of the composition, and an enteric layer representing from 5 to 30% by weight, preferably 15–20% by weight based on the total weight of the composition. The core generally includes the active principle and in an amount of from 2 to 50% preferably from 5 to 20% by weight.

In one preferred embodiment, the composition according to the invention is provided in a tablet form (single, beakable, etc.).

In another prefered embodiment, the composition is in the form of micro-tablets enclosed inside a capsule, e.g. a gelatin capsule. For this, any gelatin capsule conventionally employed in the pharmaceutical formulation field can be used, such as the hard gelatin capsule known as Capsugel, available from Eli Lilly.

The compositions of this invention are particularly suitable for oral administration of the active principles and are particularly suitable for treating gastro-intestinal sicknesses.

According to one particular embodiment, the composition according to this invention takes the form of a capsule containing 16 micro-tablets, having the following composition, expressed in mg/per capsule, starting from the core and moving outwards: lactose 50–500, active principle 10–40, hydroxypropylmethylcellulose 1–100, Polysorbate 80 or sodium lauryl sulfate 0.0–5.0, sodium stearylfumarate or magnesium stearate 0.8–8.0, crospovidone 0–50; intermediate layer: talc 0–20, titanium dioxide 0–20, silicon dioxide 0–20, hydroxypropylmethylcellulose 3–50; enteric layer: methacrylic acid copolymer, type $C_{5-50}$, triethyl citrate 0–15, talc 0–30.

The water needed to produce each component is present in an amount of from 30 to 1000 as regards the core, 10–500 as regards of the intermediate layer and 0–1000 as regards the enteric layer. It is however also possible to use another medium, such as a medium containing water and another solvent, such as alcohol.

The invention will now be described in more detail on the basis of the following examples which are only provided by way of illustrative example.

EXAMPLE 1

Preparation of a Pharmaceutical Composition of Omeprazole Intended for Oral Administration A pharmaceutical composition according to the present invention, in the form of micro-tablets contained in a gelatin capsule having the following composition, expressed in mg, was prepared.

| 1 - Composition of core: | | |
| --- | --- | --- |
|  | per microtablet | per capsule (X16 tablets.) |
| Omeprazole | 1.250 | 20.00 |
| Hydroxypropylmethylcellulose | 0.625 | 10.00 |
| Lactose | 11.875 | 190.00 |
| Sodium stearylfumarate | 0.150 | 2.40 |
| Crospovidone | 0.750 | 12.00 |
| Water | 7.500 | 120.00 |

| 2 - Composition of intermediate layer | | |
| --- | --- | --- |
|  | per microtablet | per capsule (X16 tablets.) |
| Talc | 0.375 | 6.00 |
| Titanium dioxide | 0.150 | 2.40 |
| Hydroxypropylmethylcellulose | 0.750 | 12.00 |
| Water | 5.000 | 80.00 |

| 3 - Composition of the enteric layer | | |
| --- | --- | --- |
|  | per microtablet | per capsule (X16 tablets.) |
| methacrylic acid copolymer, type C | 1.375 | 22.00 |
| triethyl citrate | 0.206 | 3.30 |
| Talc | 0.275 | 4.40 |
| Water | 3.750 | 60.00 |

First, the core is prepared by dissolving hydroxypropylmethylcellulose in water followed by addition of the omeprazole and homogenization of the resulting suspension. The omeprazole suspension thus obtained is sprayed onto lactose nuclei having a particle size of 250 $\mu$m, in a suitable fluidized bed granulator, such as a granulator sold by the companies Glatt, Aeromatic, etc. Any type of fluidized bed granulator conventionally used for this type of step can be employed with the present invention. After all the suspension has been sprayed, the nuclei are dried in a conventional manner, using, for example a fluidized bed, the temperature of the product preferably remaining below 45° C. The sodium stearylfumarate and the crospovidone are than added to the dried nuclei, followed by mixing. After this, compression of the mixture obtained is carried out to obtain microtablets of a diameter of about 2.5 mm (generally comprised between 2 and 4 mm); alternatively, compression of the mixture obtained is carried out to obtain tablets of conventional dimensions. The microtablets and the tablets contain suitable amounts of the active principle.

The intermediate layer which is prepared by dissolving the hydroxypropylmethylcellulose in water followed by addition of talc and titanium dioxide followed up by homogenization, is deposited by spraying onto the microtablets. This operation can be carried out in any suitable coating device that allows a regular film to be obtained, for example a Glatt coater with a Würster type column.

The enteric layer, which is prepared by dissolving triethyl citrate in a portion of water, with addition to aqueous dispersion of methacrylic acid copolymer of type C (Eudragit L 30D-55), followed by agitation of the mixture obtained for 30 minutes and final addition of the talc suspension that was prepared in parallel by homogenizing talc in the portion of water remaining, is deposited by spraying on the tablet coated with the intermediate layer. In order to check the stability of the microtablets prepared according to the process described above, the microtablets prepared were submitted to tests on their conservation at 45° C. in the presence of 75% relative humidity. A prior art composition sold under the name Prilosec®, was also tested. This prior art composition contains agents having an alkaline reaction. The amount of omeprazole present in the microtablets at the end of the period of storage was determined by the following process: The amount of omeprazole was determined by HPLC on a Nucleosil C18 5µ 150×4.6 mm column, using for the moving phase: buffer (8.9 g $Na_2HPO_4$, $2H_2O$ in 1000 ml of purified water; pn adjusted to 7.6 using $H_3PO_4$) in an amount of 73%/, acetonitrile in an amount of 27%. The detection consisted in measuring absorbency at 280nm.

The solution of the sample to be determines was prepared as follows. An accurately weighed amount of the microtablets, corresponding theoretically to about 20 mg of omeprazole was introduced into a gauged 50 ml flask. After adding the moving phase, this flask was placed in an ultrasound bath for 5 minutes. After the solution had returned to ambient temperature, the amount in the flask was adjusted to a volume of 50 ml by adding the moving phase. The concentration, Cd, in omeprazole, expressed nn mg/theoretical weight of microtablets is given by the following formula:

$$Cd=(Aech/Aet)\times(Pet/Pech)\times(Vd\ ech/Vd\ et)\times Pth$$

in which: Aech=area of peak of sample solution; Aet=area of peak of standard solution, this solution having been prepared under the same conditions as the sample solution but from a determined amount of omeprazole (20 mg); Pet=weight of the standard substance; Pech=weight of the sample; Vd ech=dilution factor of the sample; Vd et=dilution factor of the standard; Pth=theoretical weight of the test sample of microtablets (theoretically corresponding to 20 mg of omeprazole).

Figure 1A:
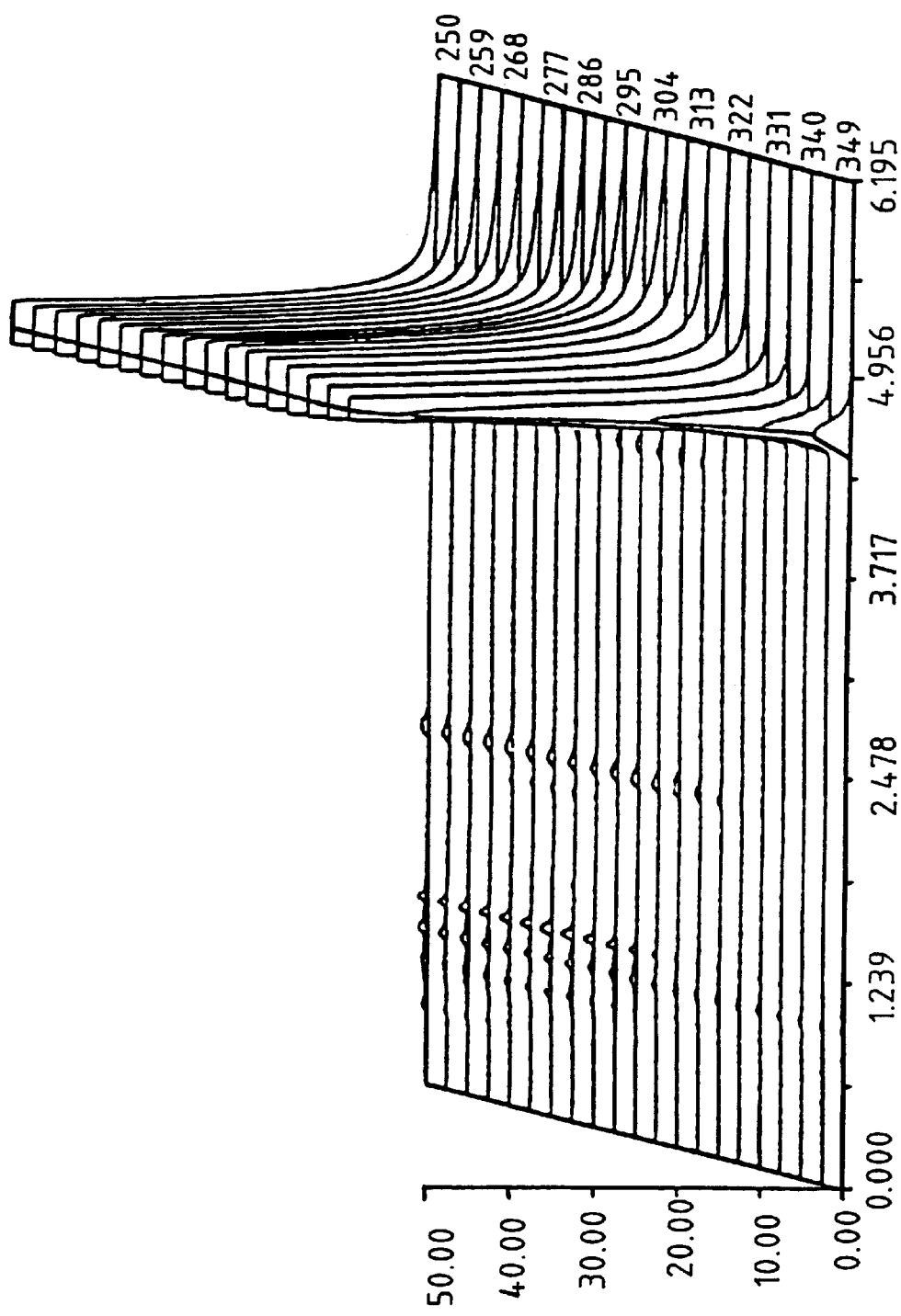
FIGS. 1(a)–(c) show the stability of the composition of example 1.
Figure 1B:
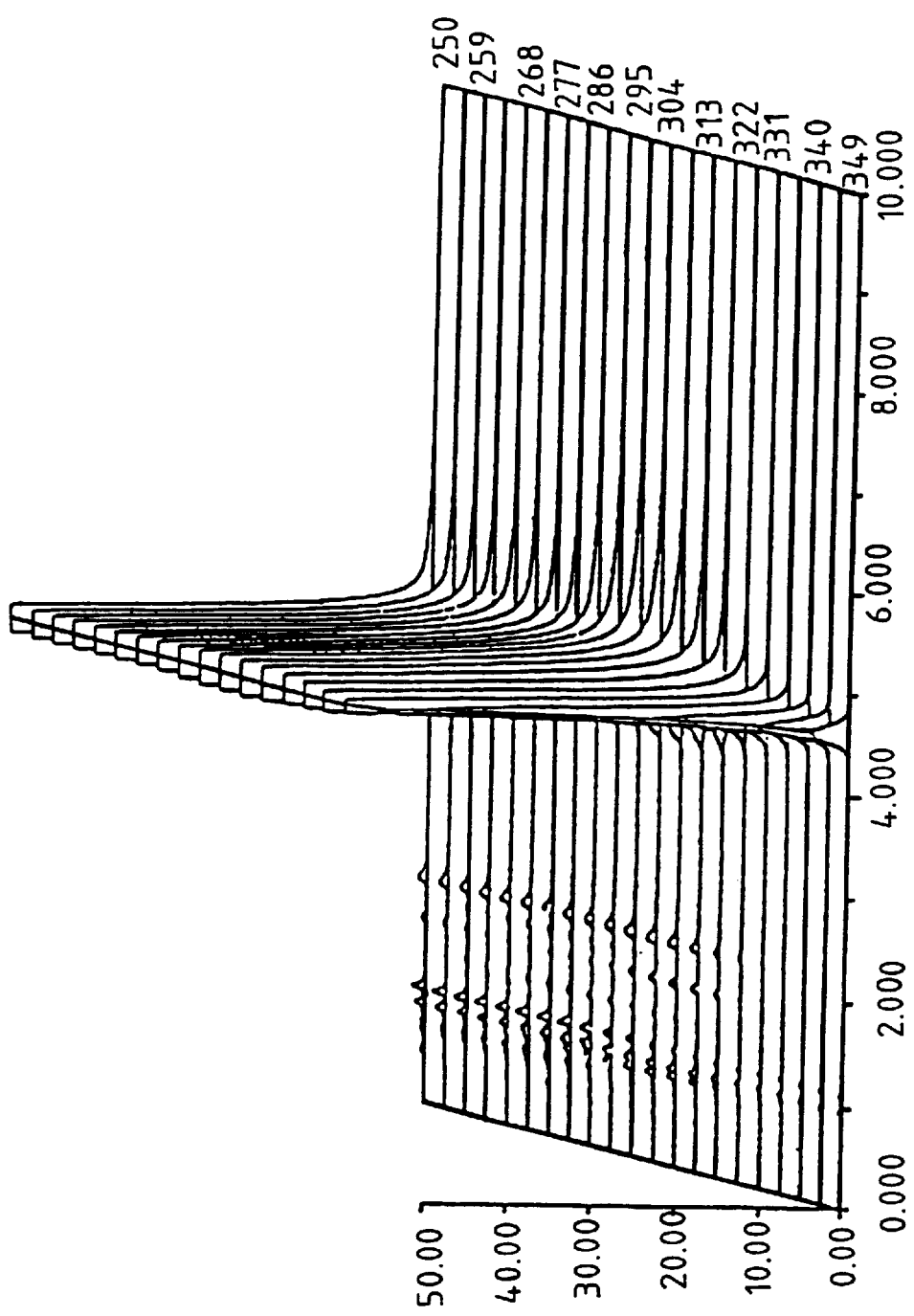
Figure 1C:
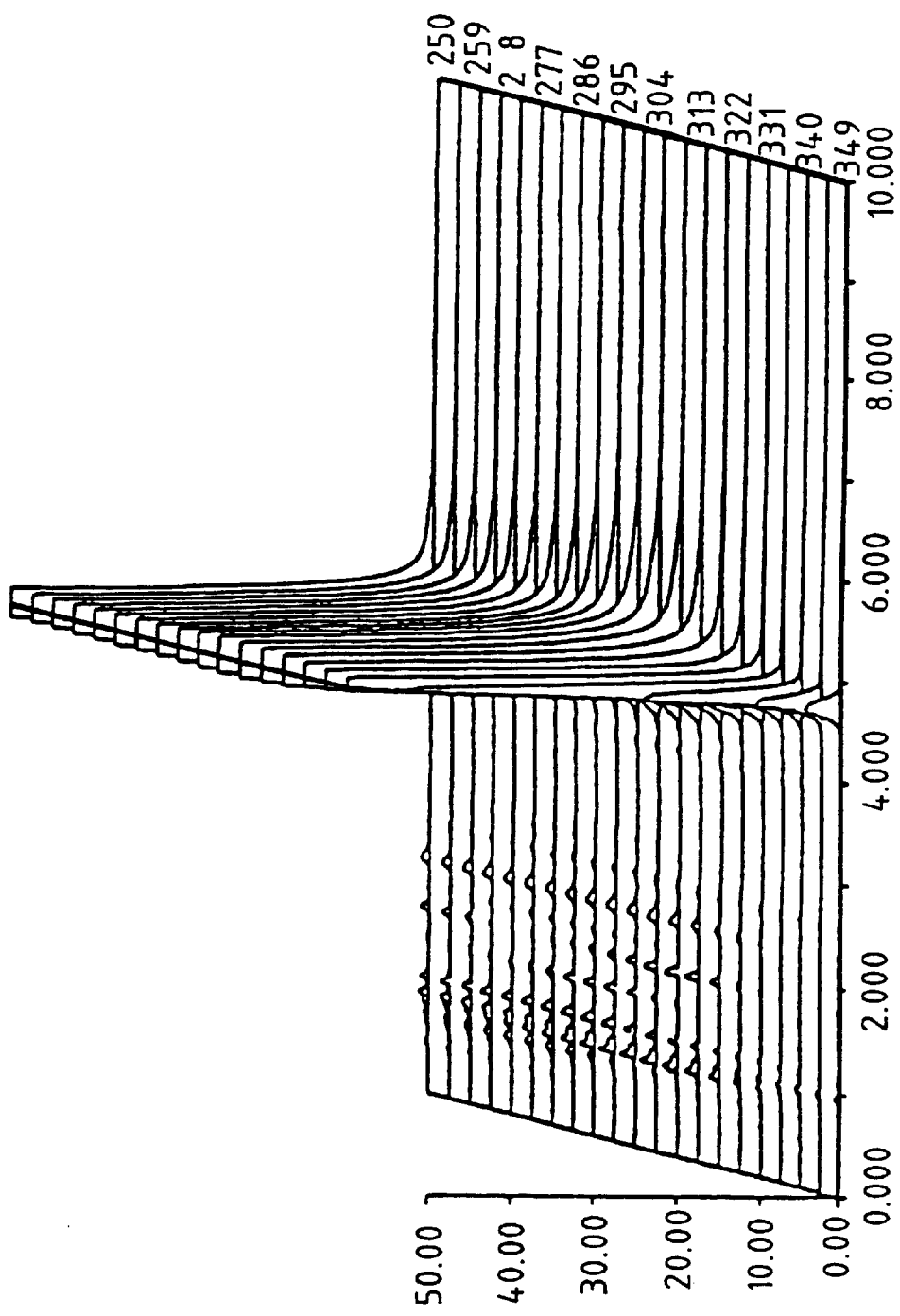
Figure 2A:
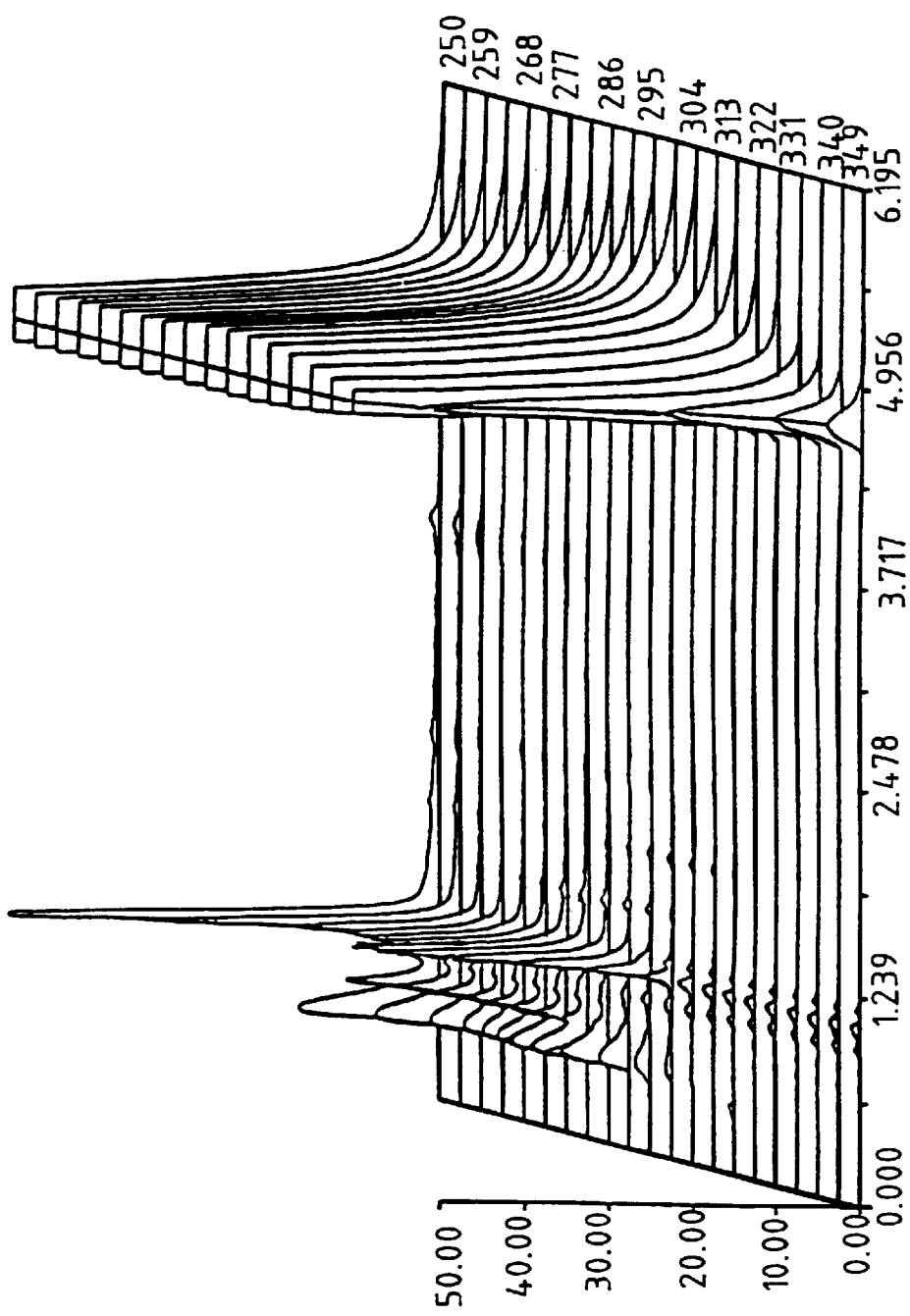
FIGS. 2(a)–(c) show the stability of a prior art composition, Prilosec®.
Figure 2B:
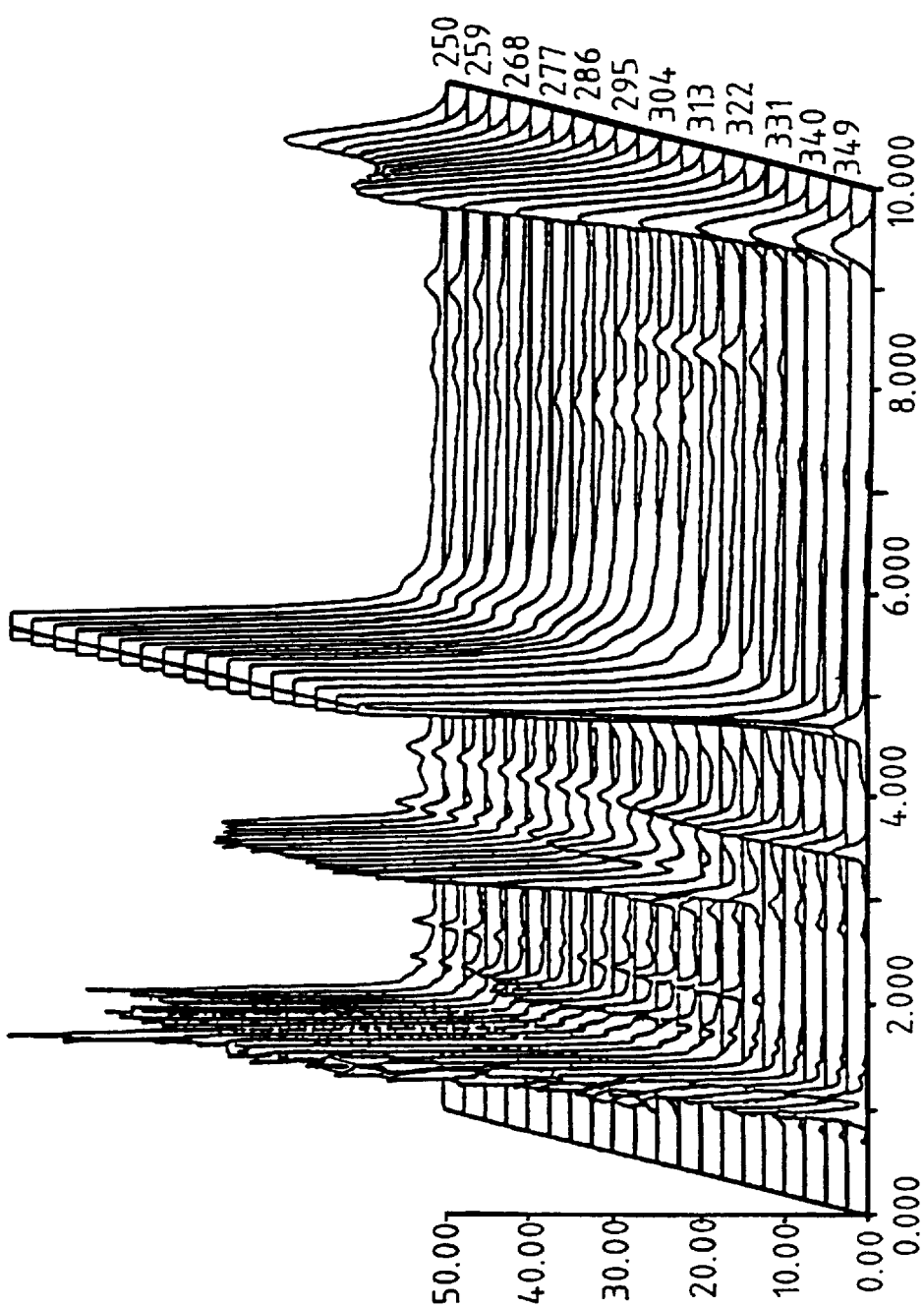
Figure 2C:
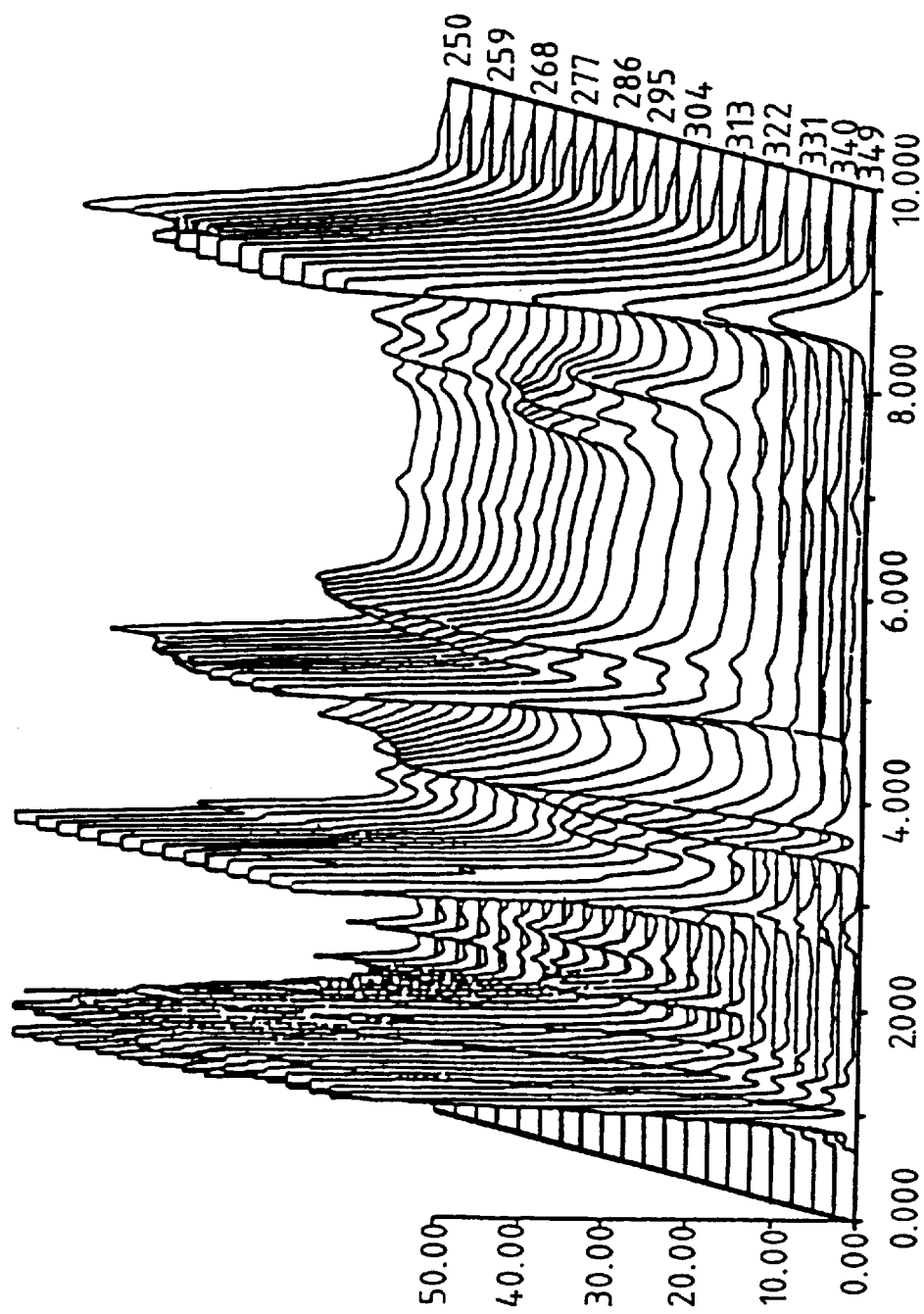

The results respectively obtained after 0 days, 14 days and 30 days are given in FIGS. 1 and 2 respectively for the composition according to the invention and for Prilosec®. Curves 1a and 2a represent the initial state, the respective percentages of the areas of the omeprazole peak being 99.67% and 97.51% for the composition according to the invention and, respectively, Prilosec®. Curves 1b and 2b show the situation after 14 days, the percentages then being 99.56% and 75.09% respectively. Curves 1c and 2c show the state after 30 days, the percentages then being 99.38% and 15.89% respectively.

EXAMPLE 2

Preparation of a Pharmaceutical Composition of Omeprazole Intended for Oral Administration A pharmaceutical composition according to the present invention in the form of microtablets contained in a gelatin capsule having the following composition expressed in mg, was prepared

| 1 - Composition of core: | | |
| --- | --- | --- |
|  | per microtablet | per capsule (X16 tablets.) |
| Omeprazole | 1.250 | 20.00 |
| Hydroxypropylmethylcellulose | 0.625 | 10.00 |
| Lactose | 11.875 | 190.00 |
| Magnesium stearate | 0.150 | 2.40 |
| Crospovidone | 0.750 | 12.00 |
| water | 7.500 | 120.00 |

| 2 - Composition of intermediate layer | | |
| --- | --- | --- |
|  | per microtablet | per capsule (X16 tablets.) |
| Talc | 0.375 | 6.00 |
| Titanium dioxide | 0.150 | 2.40 |
| Hydroxypropylmethylcellulose | 0.750 | 12.00 |
| Water | 5.000 | 80.00 |

| 3 - Composition of the enteric layer | | |
| --- | --- | --- |
|  | per microtablet | per capsule (X16 tablets.) |
| methacrylic acid copolymer, type C | 1.375 | 22.00 |
| triethyl citrate | 0.206 | 3.30 |
| Talc | 0.275 | 4.40 |
| Water | 3.750 | 60.00 |

The pharmaceutical composition was prepared according to the method described in example 1, except that the sodium stearylfumarate was replaced by magnesium stearate.

The stability of the omeprazole microtablets obtained was evaluated by the method described in example 1. The results obtained confirm those obtained for the composition according to example 1, the stability expressed as a percentage of omeprazole in the peak at 30 days being better than 99%.

EXAMPLE 3

Preparation of a Pharmaceutical Composition of Omeprazole Intended for Oral Administration A pharmaceutical composition according to the present invention in the form of microtablets contained in a gelatin capsule having the following composition expressed in mg, was prepared

| 1 - Composition of core: | | |
| --- | --- | --- |
|  | per microtablet | per capsule (X17 tablets.) |
| Omeprazole | 1.176 | 20.0 |
| Hydroxypropylmethylcellulose | 0.588 | 10.0 |
| Lactose | 6.824 | 116.0 |
| Sodium stearylfumarate | 0.103 | 1.75 |
| Crospovidone | 1.603 | 27.25 |
| water | 6.470 | 110.0 |

2 - Composition of intermediate layer

|  | per microtablet | per capsule (X17 tablets.) |
|---|---|---|
| Talc | 0.294 | 5.00 |
| Titanium dioxide | 0.118 | 2.00 |
| Hydroxypropylmethylcellulose | 0.588 | 10.0 |
| water | 4.000 | 68.0 |

3 - Composition of the enteric layer

|  | per microtablet | per capsule (X17 tablets.) |
|---|---|---|
| methacrylic acid copolymer, type C | 1.059 | 18.0 |
| triethyl citrate | 0.159 | 2.70 |
| Talc | 0.212 | 3.60 |
| Water | 4.411 | 75.0 |

The pharmaceutical composition was prepared using the method described in example 1.

The stability of the omeprazole microtablets obtained was evaluated by the method described in example 1. The results obtained confirm those obtained for the composition according to example 1.

EXAMPLE 4

Preparation of a Pharmaceutical Composition of Omeprazole Intended for Oral Administration A pharmaceutical composition according to the present invention in the form of microtablets contained in a gelatin capsule having the following composition expressed in mg, was prepared

1 - Composition of core:

|  | per microtablet | per capsule (X17 tablets.) |
|---|---|---|
| Omeprazole | 1.176 | 20.0 |
| Hydroxypropylmethylcellulose | 0.588 | 10.0 |
| Lactose | 6.824 | 116.0 |
| sodium laurylsulfate | 0.029 | 0.500 |
| sodium stearylfumarate | 0.103 | 1.75 |
| Crospovidone | 0.603 | 27.25 |
| Water | 6.470 | 110.0 |

2 - Composition of the intermediate layer

|  | per microtablet | per capsule (X17 tablets) |
|---|---|---|
| Talc | 0.294 | 5.00 |
| Titanium dioxide | 0.118 | 2.00 |
| Hydroxypropylmethylcellulose | 0.588 | 10.0 |
| Water | 4.000 | 68.0 |

3 - Composition of the enteric layer

|  | per microtablet | per capsule (X17 tablets) |
|---|---|---|
| Copolymer of methacrylic acid, type C | 1.059 | 18.0 |
| Triethyl citrate | 0.159 | 2.70 |
| Talc | 0.212 | 3.60 |
| Water | 4.411 | 75.0 |

The pharmaceutical composition was prepared using the method of example 1 except that, during the preparation of the core the sodium laurylsulfate was dissolved in water at the same time as the hydroxymethylpropylcellulose after which the omeprazole was put in suspension in this solution.

The stability of the omeprazole microtablets obtained was evaluated by the method described in example 1. The results obtained confirm those obtained for the composition of example 1.

EXAMPLE 5

Preparation of a Pharmaceutical Composition of Omeprazole Intended for Oral Administration A pharmaceutical composition according to the present invention in the form of microtablets contained in a gelatin capsule having the following composition expressed in mg, was prepared

1 - Composition of the core:

|  | per microtablet | per capsule (X17 tablets) |
|---|---|---|
| Omeprazole | 1.176 | 20.0 |
| Hydroxypropylmethylcellulose | 0.588 | 10.0 |
| Lactose | 6.824 | 116.0 |
| Polysorbate 80 | 0.029 | 0.500 |
| Sodium stearylfumarate | 0.103 | 1.75 |
| Crospovidone | 1.603 | 27.25 |
| Water | 6.470 | 110.0 |

2 - Composition of the intermediate layer

|  | per microtablet | per capsule (X17 tablets) |
|---|---|---|
| Talc | 0.294 | 5.00 |
| Titanium dioxide | 0.118 | 2.00 |
| Hydroxypropylmethylcellulose | 0.588 | 10.0 |
| Water | 4.000 | 68.0 |

3 - Composition of the enteric layer

|  | per microtablet | per capsule (X17 tablets) |
|---|---|---|
| Methacrylic.acid, copolymer type C | 1.059 | 18.0 |
| Triethyl citrate | 0.159 | 2.70 |
| Talc | 0.212 | 3.60 |
| Water | 4.411 | 75.0 |

The pharmaceutical composition was prepared using the method described in example 1, except for the fact that during preparation of the core, Polysorbate 80 was dissolved in water at the same time as the hydroxymethylpropylcellulose after which the omeprazole was put in suspension in this solution.

The stability of the omeprazole microtablets (measured as in example 1) confirmed the results obtained for the composition according to example 1.

EXAMPLES 6 to 8

Preparation of Pharmaceutical Compositions of Pantoprazole for Oral Administration The pharmaceutical compositions according to the invention in the form of individual tablets containing 40 mg of pantoprazole active principle having the following composition expressed in mg/tablet were prepared.

1 - Composition of the core:

|  | Ex. No.6 | Ex. No.7 | Ex. No.8 |
|---|---|---|---|
| Pantoprazole | 40.00 | 40.00 | 40.00 |
| Hydroxypropylmethylcellulose | 20.00 | 20.00 | 20.00 |
| Lactose | 120.00 | 120.00 | 120.00 |
| Polysorbate 80 | — | 1.00 | — |
| Sodium laurylsulfate | — | — | 1.00 |
| Sodium stearylfumarate | 1.00 | 1.00 | 1.00 |
| Crospovidone | 20.00 | 20.00 | 20.00 |
| Water | 250.0 | 250.0 | 250.0 |

2 - Composition of the intermediate layer

|  | Ex. No.6 | Ex. No.7 | Ex. No.8 |
|---|---|---|---|
| Talc | 2.5 | 2.5 | 2.5 |
| Titanium dioxide | 1.0 | 1.0 | 1.0 |
| Hydroxypropylmethylcellulose | 5.0 | 5.0 | 5.0 |
| Water | 35.0 | 35.0 | 35.0 |

3 - Composition of the enteric layer

|  | Ex. No.6 | Ex. No.7 | Ex. No.8 |
|---|---|---|---|
| Methacrylic acid copolymer, type C | 10.00 | 10.00 | 10.00 |
| triethyl citrate | 1.5 | 1.5 | 1.5 |
| Talc | 2.0 | 2.0 | 2.0 |
| Water | 40.0 | 40.0 | 40.0 |

The pharmaceutical composition was prepared using the method described in example 1, except that firstly, during preparation of the core of the compositions of examples 7 and 8, Polysorbate 80 and, respectively, sodium lauryl sulfate were dissolved in the water at the same time as the hydroxymethylpropylcellulose after which the pantoprazole was put into the suspension in the solution and, secondly, the final composition was obtained in the form of tablets, and not microtablets contained in a capsule.

The stability of the pantoprazole tablets obtained was evaluated by the method described in example 1. The results obtained confirm those obtained for the composition according to example 1.

EXAMPLES 9–11

Preparation of Pharmaceutical Composition of Lansoprazole for Oral Administration Pharmaceutical compositions according to the present invention, in the form of microtablets contained in a gelatin capsule, having the following composition expressed in mg/capsule were prepared.

1 - Composition of the core:

|  | Ex. No.9 | Ex. No.10 | Ex. No.11 |
|---|---|---|---|
| lanzoprazole | 30.00 | 30.00 | 30.00 |
| Hydroxypropylmethylcellulose | 15.00 | 15.00 | 15.00 |
| Lactose | 120.00 | 120.00 | 120.00 |
| Polysorbate 80 | — | 0.75 | — |
| Sodium laurylsulfate | — | — | 0.75 |
| Sodium stearylfumarate | 1.25 | 1.25 | 1.25 |
| Crospovidone | 20.00 | 20.00 | 20.00 |
| Water | 200.0 | 200.0 | 200.0 |

2 - Composition of the intermediate layer

|  | Ex. No.6 | Ex. No.7 | Ex. No.8 |
|---|---|---|---|
| Talc | 5.0 | 5.0 | 5.0 |
| Titanium dioxide | 2.0 | 2.0 | 2.0 |
| Hydroxypropylmethylcellulose | 10.0 | 10.0 | 10.0 |
| Water | 68.0 | 68.0 | 68.0 |

3 - Composition of the enteric layer

|  | Ex. No.9 | Ex. No.10 | Ex. No.11 |
|---|---|---|---|
| Methacrylic acid copolymer, type C | 18.0 | 10.0 | 10.0 |
| Triethyl citrate | 2.7 | 2.7 | 2.7 |
| Talc | 3.6 | 3.6 | 3.6 |
| Water | 75.0 | 75.0 | 75.0 |

The pharmaceutical composition was prepared using the method described in example 1, except that firstly, during preparation of the core of the compositions of examples 10 and 11, Polysorbate 80 and, respectively, sodium lauryl sulfate were dissolved in the water at the same time as the hydroxymethylpropylcellulose after which the pantoprazole was put to the suspension in the solution.

The stability of the pantoprazole tablets obtained was evaluated by the method described in example 1. The results obtained confirm those obtained for the composition according to example 1.

EXAMPLE 12

Preparation of Pharmaceutical Composition of Omeprazole for Oral Administration

A pharmaceutical composition according to the present invention, in the form of microtablets contained in a gelatin capsule, having the following composition expressed in mg/was prepared

1 - Composition of the core:

|  | per microtablet | per capsule (X17 tablets) |
|---|---|---|
| Omeprazole | 1.176 | 20.0 |
| Hydroxypropylmethylcellulose | 0.588 | 10.0 |
| Lactose | 6.823 | 116.0 |
| Polyplasdone XL | 1.603 | 27.25 |
| Sodium stearylfumarate | 0.103 | 1.75 |
| Water | 6.471 | 110.0 |

2 - Composition of the intermediate layer

|  | per microtablet | per capsule (X17 tablets) |
|---|---|---|
| Talc (micronized) | 0.176 | 3.00 |
| Titanium dioxide | 0.118 | 2.00 |
| Hydroxypropylmethylcellulose | 0.588 | 10.0 |
| Silicon dioxide | 0.088 | 1.50 |
| Water | 5.588 | 95.00 |

3 - Composition of the enteric layer

|  | per microtablet | per capsule (X17 tablets) |
|---|---|---|
| Eudragit L 30D 55 (solid) | 1.059 | 18.0 |
| Triethyl citrate | 0.159 | 2.70 |
| Talc (micronized) | 0.212 | 3.60 |
| Water | 4.412 | 75.0 |

The pharmaceutical composition was prepared using the method described in the examples above.

The stability of the microtablets of omeprazole (measures like in example 1) confirm the results obtained for the composition according to example 1.

EXAMPLE 13

Preparation of a Pharmaceutical Composition of Omeprazole for Oral Administration A pharmaceutical composition according to the present invention, in the form of microtablets contained in a gelatin capsule, having the following composition expressed in mg/was prepared

1 - Composition of the core:

|  | per microtablet | per capsule (X17 tablets) |
|---|---|---|
| Omeprazole | 1.176 | 20.0 |
| Hydroxypropylmethylcellulose | 0.588 | 10.0 |
| Lactose | 6.823 | 116.0 |
| Polyplasdone XL | 1.603 | 27.25 |
| Glyceryl behenate | 0.103 | 1.75 |
| Water | 6.471 | 110.0 |

2 - Composition of the intermediate layer

|  | per microtablet | per capsule (X17 tablets) |
|---|---|---|
| Talc (micronized) | 0.176 | 3.00 |
| Titanium dioxide | 0.118 | 2.00 |
| Hydroxypropylmethylcellulose | 0.588 | 10.0 |
| Silicon dioxide | 0.088 | 1.50 |
| Water | 5.588 | 95.00 |

3 - Composition of the enteric layer

|  | per microtablet | per capsule (X17 tablets) |
|---|---|---|
| Eudragit L 30D 55 (solid) | 1.059 | 18.0 |
| Triethyl citrate | 0.159 | 2.70 |
| Talc (micronized) | 0.212 | 3.60 |
| Water | 4.412 | 75.0 |

The pharmaceutical composition was prepared using the process described for the examples above.

The stability of the microtablets of omeprazole (measures like in example 1) confirm the results obtained for the composition according to example 1.

EXAMPLE 14

Preparation of Pharmaceutical Composition of Omeprazole for Oral Administration

A pharmaceutical composition according to the present invention, in the form of microtablets contained in a gelatin capsule, having the following composition expressed in mg/was prepared

1 - Composition of the core:

|  | per microtablet | per capsule (X17 tablets) |
|---|---|---|
| Omeprazole | 1.176 | 20.0 |
| Hydroxypropylmethylcellulose | 0.588 | 10.0 |
| Lactose | 6.823 | 116.0 |
| Polyplasdone XL | 1.603 | 27.25 |
| Talc (micronized) | 0.103 | 1.75 |
| Water | 6.471 | 110.0 |

2 - Composition of the intermediate layer

|  | per microtablet | per capsule (X17 tablets) |
|---|---|---|
| Talc (micronized) | 0.176 | 3.00 |
| Titanium dioxide | 0.118 | 2.00 |
| Hydroxypropylmethylcellulose | 0.588 | 10.0 |
| Silicon dioxide | 0.088 | 1.50 |
| Water | 5.588 | 95.00 |

| 3 - Composition of the enteric layer | | |
|---|---|---|
| | per microtablet | per capsule (X17 tablets) |
| Eudragit L 30D 55 (solid) | 1.059 | 18.0 |
| Triethyl citrate | 0.159 | 2.70 |
| Talc (micronized) | 0.212 | 3.60 |
| Water | 4.412 | 75.0 |

The pharmaceutical composition was prepared using the process described for the examples above.

The stability of the microtablets of omeprazole (measures like in example 1) confirm the results obtained for the composition according to example 1.

EXAMPLES 15–17

Preparation of Pharmaceutical Composition of Lansoprazole for Oral Administration Pharmaceutical composition according to the present invention, in the form of microtablets contained in a gelatin capsule, having the following composition expressed in mg/capsule were prepared.

| 1- Composition of the core: | | | |
|---|---|---|---|
| | Ex. No. 15 | Ex. No. 16 | Ex. No. 17 |
| lanzoprazole | 30.00 | 30.00 | 30.00 |
| Hydroxypropylmethylcellulose | 15.00 | 15.00 | 15.00 |
| Lactose | 120.00 | 120.00 | 120.00 |
| Polysorbate 80 | — | 0.75 | — |
| Sodium laurylsulfate | — | — | 0.75 |
| Glyceryl behenate | 1.25 | 1.25 | 1.25 |
| Crospovidone | 20.00 | 20.00 | 20.00 |
| Water | 200.0 | 200.0 | 200.0 |

| 2- Composition of the intermediate layer | | | |
|---|---|---|---|
| | Ex. No. 15 | Ex. No. 16 | Ex. No. 17 |
| Talc | 5.0 | 5.0 | 5.0 |
| Titanium dioxide | 2.0 | 2.0 | 2.0 |
| Hydroxypropylmethylcellulose | 10.0 | 10.0 | 10.0 |
| Water | 68.0 | 68.0 | 68.0 |

| 3- Composition of the enteric layer | | | |
|---|---|---|---|
| | Ex. No. 15 | Ex. No. 16 | Ex. No. 17 |
| Methacrylic acid copolymer, type C | 18.0 | 10.0 | 10.0 |
| Triethyl citrate | 2.7 | 2.7 | 2.7 |
| Talc | 3.6 | 3.6 | 3.6 |
| Water | 75.0 | 75.0 | 75.0 |

The pharmaceutical composition was prepared by the method described in examples 9 to 11, except that, during preparation of the core, glyceryl behenate was employed instead of sodium stearyl fumarate.

The stability of the microtablets of lansoprazole (measures like in example 1) confirm the results obtained for the composition according to example 1.

Examples 18–20

Preparation of Pharmaceutical Composition of Lansoprazole for Oral Administration Pharmaceutical compositions according to the present invention, in the form of microtablets contained in a gelatin capsule, having the following composition expressed in mg/capsule were prepared.

| 1- Composition of the core: | | | |
|---|---|---|---|
| | Ex. No. 18 | Ex. No. 19 | Ex. No. 20 |
| lanzoprazole | 30.00 | 30.00 | 30.00 |
| Hydroxypropylmethylcellulose | 15.00 | 15.00 | 15.00 |
| Lactose | 120.00 | 120.00 | 120.00 |
| Polysorbate 80 | — | 0.75 | — |
| Sodium laurylsulfate | — | — | 0.75 |
| Talc (micronized) | 1.25 | 1.25 | 1.25 |
| Crospovidone | 20.00 | 20.00 | 20.00 |
| Water | 200.0 | 200.0 | 200.0 |

| 2- Composition of the intermediate layer | | | |
|---|---|---|---|
| | Ex. No. 18 | Ex. No. 19 | Ex. No. 20 |
| Talc | 5.0 | 5.0 | 5.0 |
| Titanium dioxide | 2.0 | 2.0 | 2.0 |
| Hydroxypropylmethylcellulose | 10.0 | 10.0 | 10.0 |
| Water | 68.0 | 68.0 | 68.0 |

| 3- Composition of the enteric layer | | | |
|---|---|---|---|
| | Ex. No. 18 | Ex. No. 19 | Ex. No. 20 |
| Methacrylic acid copolymer, type C | 18.0 | 10.0 | 10.0 |
| Triethyl citrate | 2.7 | 2.7 | 2.7 |
| Talc | 3.6 | 3.6 | 3.6 |
| Water | 75.0 | 75.0 | 75.0 |

The pharmaceutical composition was prepared by the method described in examples 9 to 11, except that, during preparation of the core, micronized talc was employed instead of sodium stearyl fumarate.

The stability of the microtablets of lansoprazole (measures like in example 1) confirm the results obtained for the composition according to example 1.

EXAMPLES 21–23

Preparation of Pharmaceutical Compositions of Pantoprazole for Oral Administration The pharmaceutical compositions according to the invention in the form of individual tablets containing 40 mg of pantoprazole active principle having the following composition expressed in mg/tablet were prepared.

1- Composition of the core:

| | Ex. No. 21 | Ex. No. 22 | Ex. No. 23 |
|---|---|---|---|
| Pantoprazole | 40.00 | 40.00 | 40.00 |
| Hydroxypropylmethylcellulose | 20.00 | 20.00 | 20.00 |
| Lactose | 120.00 | 120.00 | 120.00 |
| Polysorbate 80 | — | 1.00 | — |
| sodium laurylsulfate | — | — | 1.00 |
| Glyceryl behenate | 1.00 | 1.00 | 1.00 |
| Crospovidone | 20.00 | 20.00 | 20.00 |
| Water | 250.0 | 250.0 | 250.0 |

2- Composition of the intermediate layer

| | Ex. No. 21 | Ex. No. 22 | Ex. No. 23 |
|---|---|---|---|
| Talc | 2.5 | 2.5 | 2.5 |
| Titanium dioxide | 1.0 | 1.0 | 1.0 |
| Hydroxypropylmethylcellulose | 5.0 | 5.0 | 5.0 |
| Water | 35.0 | 35.0 | 35.0 |

3- Composition of the enteric layer

| | Ex. No. 21 | Ex. No. 22 | Ex. No. 23 |
|---|---|---|---|
| Methacrylic acid copolymer, type C | 10.00 | 10.00 | 10.00 |
| Triethyl citrate | 1.5 | 1.5 | 1.5 |
| Talc | 2.0 | 2.0 | 2.0 |
| Water | 40.0 | 40.0 | 40.0 |

The pharmaceutical composition was prepared by the method described in examples 6 to 8, except that, during preparation of the core, glyceryl behenate was employed instead of sodium stearyl fumarate.

The stability of the microtablets of pantoprazole (measured like in example 1) confirms the results obtained for the composition according to example 1.

EXAMPLES 24–26

Preparation of Pharmaceutical Compositions of Pantoprazole for Oral Administration The pharmaceutical compositions according to the invention in the form of individual tablets containing 40 mg of pantoprazole active principle having the following composition expressed in mg/tablet were prepared.

1- Composition of the core:

| | Ex. No. 24 | Ex. No. 25 | Ex. No. 26 |
|---|---|---|---|
| Pantoprazole | 40.00 | 40.00 | 40.00 |
| Hydroxypropylmethylcellulose | 20.00 | 20.00 | 20.00 |
| Lactose | 120.00 | 120.00 | 120.00 |
| Polysorbate 80 | — | 1.00 | — |
| Sodium laurylsulfate | — | — | 1.00 |
| Talc (micronized) | 1.00 | 1.00 | 1.00 |
| Crospovidone | 20.00 | 20.00 | 20.00 |
| Water | 250.0 | 250.0 | 250.0 |

2- Composition of the intermediate layer

| | Ex. No. 24 | Ex. No. 25 | Ex. No. 26 |
|---|---|---|---|
| Talc | 2.5 | 2.5 | 2.5 |
| Titanium dioxide | 1.0 | 1.0 | 1.0 |
| Hydroxypropylmethylcellulose | 5.0 | 5.0 | 5.0 |
| Water | 35.0 | 35.0 | 35.0 |

3- Composition of the enteric layer

| | Ex. No. 24 | Ex. No. 25 | Ex. No. 26 |
|---|---|---|---|
| Methacrylic acid copolymer, type C | 10.00 | 10.00 | 10.00 |
| Triethyl citrate | 1.5 | 1.5 | 1.5 |
| Talc | 2.0 | 2.0 | 2.0 |
| Water | 40.0 | 40.0 | 40.0 |

The pharmaceutical composition was prepared by the method described in examples 6 to 8, except that, during preparation of the core, micronized talc was employed instead of sodium stearyl fumarate.

The stability of the microtablets of pantoprazole (measured like in example 1) confirms the results obtained for the composition according to example 1.

COMPARATIVE EXAMPLE

The instant micro-tablet of example 1 are recompressed in a microcrystalline cellulose matrix using the general procedure described in the examples of WO96/01624. The resulting tablets show cracks on their surfaces, evidencing that recompression of the microtablets of the invention according to the procedure described in the WO96/01624 patent is not successful in producing suitable tablets.

Further, said final tablets have been tested as to their dissolution in a 0.1N HCl solution, according to the general procedure described in WO96/01624. Results show that after 2 hours, the dissolution is about 55%, evidencing that said final tablets cannot withstand acidic conditions.

It is clear that the particular pharmaceutical excipients described in the compositions of examples 1 to 26 can be replaced by other pharmaceutical excipients having the same function and which are conventionally employed in the pharmaceutical formulation field, provided that they are chemically compatible with the active principle.

All such alternative embodiments are covered by the scope of the invention to the extent where the stability of the resulting pharmaceutical composition is not substantially affected.

The teaching of the invention extends in fact to any of the acid-labile active principles mentioned in the introductory part of this specification, and notably those of the preferred embodiments and from the examples from the prior art. The mixing (e.g. coating, pure mixing or granulating) step of the process according to the invention can be carried out using any known technique conventionally used for this purpose. Examples which can be mentioned are coating by immersion, dry coating, dry mixing, spray coating, spray mixing, etc.

Finally, it should be noted that additional layers or sub-layers can be added, for the purposes of adding flavor and/or color, and/or improving acceptability of the medicament and/or allowing it to be marked.

What is claimed is:

1. A process for preparing a composition exempt of alkaline-reacting compounds comprising:
    (a) a core containing an acid-labile omeprazole active principle, said core comprising pharmaceutically inert nuclei and said active ingredient granulated together and then compressed together, and said omeprazole active principle being in a form different form an alkaline salt;
    (b) an intermediate layer; and
    (c) an enteric layer, comprising the steps of
        (i) granulating nuclei with the active principle;
        (ii) compressing the product of step (i) to form a core containing the active principle;
        (iii) coating said core with the intermediate layer; and
        (iv) coating a product from step (iii) with the enteric layer.

2. The process according to claim 1, in which step (i) is performed by spraying a medium containing the active principle onto nuclei in a fluidized bed granulator followed by drying the product thus obtained.

3. The process according to claim 2, in which the medium containing the active principle is an aqueous medium.

4. The process according to claim 1, in which said nuclei have a particle size, in the absence of the active principle, comprised between 80 and 500 μm.

5. The process according to claim 1, in which said nuclei have a particle size, in the absence of the active principle, comprised between 150 and 300 μm.

6. The process according to claim 5, additionally comprising the step of mixing the product of step (i) with at least one lubricant.

7. The process according to claim 6, wherein said lubricant is selected from the group consisting of sodium stearylfumrate, magnesium stearate, glyceryl behenate, and talc.

8. The process according to claim 1, in which the intermediate layer comprises silicon dioxide.

9. The process according to claim 3, in which said nuclei have a particle size, in the absence of the active principle, comprised between 80 and 500 μm.

10. The process according to claim 9, in which said nuclei have a particle size, in the absence of the active principle, comprised between 150 and 300 μm.

11. A stable drug composition exempt of alkaline-reactinq compounds comprising:
    (a) a core containing all acid-labile omeprazole active principle, said core comprising pharmaceutical inert nuclei and said active ingredient granulated together and then compressed together and said omeprazole active principle being in a form different from an alkaline salt;
    (b) an intermediate layer; and
    (c) an enteric layer, wherein the composition is obtained by a process comprising the steps of:
        (i) granulating nuclei with an active principle;
        (ii) compressing the product of step (i) to form a core containing the active principle;
        (iii) coating said core with an intermediate layer; and
        (iv) coating a product from step (iii) with an enteric layer.

12. The composition according to claim 7, in which step (i) is carried out by spraying a medium containing an active principle onto nuclei in a fluidized bed granulator followed by drying the product thus obtained.

13. The composition according to claim 12, in which the medium containing the active principle is an aqueous medium.

14. The composition according to claim, 12, in which said nuclei have a particle size, in the absence of the active principle, comprised between 80 and 500 μm.

15. The composition according to claim 14, in which said nuclei have a particle size, in the absence of the active principle, comprised between 150 and 300 μm.

16. The process according to claim 13, in which said nuclei have a particle size, in the absence of the active principle, comprised between 80 arid 500 μm.

17. The process according to claim 16, in which said nuclei have a particle size, in the absence of the active principle, comprised between 150 and 300 μm.

18. The composition according to claim 11, in which at least one lubricant is additionally present with said nuclei and said active ingredient.

19. The composition according to claim 10 wherein said lubricant is selected from the group consisting of sodium stearylfumarate, magnesium stearate, glyceryl behenate, and talc.

20. The composition according to claim 11, in which the intermediate layer contains silicon dioxide.

21. The composition according to claim 16, in which at least one lubricant, is additionally present with said nuclei and said active ingredient.

22. The composition according to claim 21, wherein said lubricant is selected from the group consisting of sodium stearylfumarate, magnesium stearate, glyceryl behenate, and talc.

23. The composition according to claim 16, in which the intermediate layer contains silicon dioxide.

24. The composition according to claim 11, provided in a tablet form.

25. The composition according to claim 13, provided in a table form.

26. The composition according to claim 15, provided in a tablet form.

27. The composition according to claim 17, provided in a tablet form.

28. The composition according to claim 11, provided in the form of microtablets enclosed inside a capsule.

29. The composition according to claim 13, provided in the form of microtablets enclosed inside a capsule.

30. The composition according to claim 15, provided in the form of microtablets enclosed inside a capsule.

31. The composition according to claim 17, provided in the form of microtablets enclosed inside a capsule.

* * * * *